(12) United States Patent
O'Neill et al.

(10) Patent No.: US 10,631,736 B2
(45) Date of Patent: Apr. 28, 2020

(54) REUSABLE MR SAFE TEMPERATURE PROBE FOR SURFACE AND BODY TEMPERATURE MEASUREMENT

(71) Applicant: KONINKLIJKE PHILIPS N.V., Eindhoven (NL)

(72) Inventors: Francis Patrick O'Neill, Kissimmee, FL (US); Leonard John Kovalsky, Orlando, FL (US); Ivars Ivanov, Orlando, FL (US); Steven Andrew Kaspick, Orlando, FL (US); Michael Gemmati, Orlando, FL (US); Kevin Jirka, Orlando, FL (US); John Weinacht, Oviedo, FL (US); Frederic Emmanuel Borne, Quebec (CA); Maxim Vachon-Savary, Quebec (CA)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 432 days.

(21) Appl. No.: 14/649,583

(22) PCT Filed: Dec. 10, 2013

(86) PCT No.: PCT/IB2013/060765
§ 371 (c)(1),
(2) Date: Jun. 4, 2015

(87) PCT Pub. No.: WO2014/097049
PCT Pub. Date: Jun. 26, 2014

(65) Prior Publication Data
US 2015/0313473 A1    Nov. 5, 2015

Related U.S. Application Data

(60) Provisional application No. 61/738,460, filed on Dec. 18, 2012.

(51) Int. Cl.
*A61B 5/00* (2006.01)
*A61B 5/01* (2006.01)
*A61B 5/055* (2006.01)

(52) U.S. Cl.
CPC ............... *A61B 5/01* (2013.01); *A61B 5/055* (2013.01)

(58) Field of Classification Search
CPC ......... A61B 51/01; A61B 5/055; A61B 90/39; A61B 2090/3954; G01K 13/002; G01R 33/285
See application file for complete search history.

(56) References Cited

U.S. PATENT DOCUMENTS

| | | |
|---|---|---|
| 3,190,436 A | 6/1965 | Diamant |
| 3,315,797 A | 4/1967 | Olsson |

(Continued)

FOREIGN PATENT DOCUMENTS

| | | | |
|---|---|---|---|
| EP | 0336984 A1 * | 10/1989 | ......... A61B 5/14539 |
| WO | 0223148 A1 | 3/2002 | |
| WO | 2010102117 A1 | 9/2010 | |

OTHER PUBLICATIONS

Somnex, "MRI active guidewire with an embedded temperature probe and providing a distinct tip signal to enhance clinical safety", Jounal of Cardiovascular Magnetic Resonance 12:38, 2012 (Year: 2012).*

(Continued)

*Primary Examiner* — Joanne M Hoffman (57) ABSTRACT

A magnetic resonance probe (2) includes a fiber optic sensor probe (32) and a sheath (38). The fiber optic sensor probe (32) includes a non-ferrous sensor (42) on a distal portion (36) configured for insertion into a subject, a locking element (34) connected to the distal portion (36), and a proximal portion (44) connected to the locking element (34) and in light communication via an optical fiber (48) with the (Continued)

non-ferrous sensor (42) and includes a connector (46). The sheath (38) covers the distal portion (36) of the fiber optic sensor probe (32), engages the locking element (34), and provides a sterile outer surface (70).

14 Claims, 9 Drawing Sheets (56) References Cited

U.S. PATENT DOCUMENTS

| | | | | |
|---|---|---|---|---|
| 3,552,558 | A * | 1/1971 | Poncy | G01K 1/083 206/306 |
| 3,732,975 | A * | 5/1973 | Poncy | G01K 1/083 206/212 |
| 3,752,309 | A * | 8/1973 | Hopkins | G01K 1/083 206/306 |
| 3,822,593 | A | 7/1974 | Oudewaal | |
| 4,026,751 | A * | 5/1977 | Fowler | G01K 1/08 156/290 |
| D252,104 | S | 6/1979 | Nagy et al. | |
| 4,165,000 | A * | 8/1979 | Poncy | G01K 1/083 206/306 |
| 4,306,562 | A * | 12/1981 | Osborne | A61M 25/0668 604/164.05 |
| 4,392,005 | A * | 7/1983 | Mohrman | G01K 13/002 136/221 |
| 4,402,685 | A * | 9/1983 | Buhler | A61L 29/049 525/931 |
| 4,449,973 | A * | 5/1984 | Luther | A61M 25/065 604/161 |
| 4,596,559 | A * | 6/1986 | Fleischhacker | A61M 25/0668 604/161 |
| D300,609 | S | 4/1989 | Leverty | |
| 4,911,559 | A | 3/1990 | Meyst et al. | |
| 4,983,168 | A * | 1/1991 | Moorehead | A61M 25/0668 604/161 |
| RE33,854 | E * | 3/1992 | Adair | A61B 1/00101 600/109 |
| 5,167,634 | A * | 12/1992 | Corrigan, Jr. | A61M 25/0668 604/160 |
| 5,221,263 | A * | 6/1993 | Sinko | A61M 25/0668 604/161 |
| 5,273,041 | A * | 12/1993 | Richards | A61B 5/055 600/411 |
| 5,280,173 | A | 1/1994 | Morse et al. | |
| 5,383,453 | A * | 1/1995 | Fischer | A61B 5/14539 29/428 |
| 5,588,432 | A * | 12/1996 | Crowley | A61B 5/02007 600/374 |
| 5,713,867 | A * | 2/1998 | Morris | A61M 25/0668 604/164.05 |
| 5,738,632 | A * | 4/1998 | Karasawa | G01R 33/285 324/318 |
| 5,771,327 | A * | 6/1998 | Bar-Or | G02B 6/3849 385/139 |
| 5,930,440 | A * | 7/1999 | Bar-Or | G02B 6/241 385/136 |
| 5,997,562 | A * | 12/1999 | Zadno-Azizi | A61M 25/0662 604/158 |
| 6,216,030 | B1 * | 4/2001 | Howard | A61M 25/0105 600/427 |
| 6,358,460 | B1 * | 3/2002 | Hunt, Jr. | B29D 23/001 264/491 |
| 6,454,744 | B1 * | 9/2002 | Spohn | A61M 25/0668 604/164.05 |
| 6,463,187 | B1 * | 10/2002 | Baruch | A61B 5/021 385/12 |
| 6,574,497 | B1 | 6/2003 | Pacetti | |
| 6,716,223 | B2 * | 4/2004 | Leopold | A61M 25/0668 606/144 |
| 6,738,145 | B2 | 5/2004 | Sherrer et al. | |
| 7,011,647 | B2 | 3/2006 | Purdy et al. | |
| 7,048,732 | B2 | 5/2006 | Ellingsen | |
| 7,160,291 | B2 * | 1/2007 | Damasco | A61B 18/02 606/20 |
| 7,187,964 | B2 * | 3/2007 | Khoury | A61B 5/0422 600/509 |
| 7,684,657 | B2 | 3/2010 | Donlagic et al. | |
| 7,720,532 | B2 * | 5/2010 | Hashimshony | A61B 34/20 600/439 |
| 7,762,995 | B2 | 7/2010 | Eversull et al. | |
| 9,360,643 | B2 * | 6/2016 | Rinzler | G02B 6/3813 |
| 2001/0038453 | A1 * | 11/2001 | Jung | G01J 3/02 356/419 |
| 2002/0022832 | A1 | 2/2002 | Mikus et al. | |
| 2002/0029054 | A1 * | 3/2002 | Rabiner | A61B 17/320068 606/169 |
| 2002/0147394 | A1 * | 10/2002 | Ellingsen | A61B 5/01 600/410 |
| 2002/0159671 | A1 | 10/2002 | Boyd et al. | |
| 2004/0122494 | A1 * | 6/2004 | Eggers | A61B 18/04 607/103 |
| 2004/0186377 | A1 | 9/2004 | Zhong et al. | |
| 2004/0236314 | A1 * | 11/2004 | Saab | A61M 39/0247 604/539 |
| 2005/0177025 | A1 * | 8/2005 | Jaker | A61B 1/00135 600/121 |
| 2005/0194979 | A1 * | 9/2005 | Roman | G01R 31/1272 324/536 |
| 2005/0195402 | A1 | 9/2005 | May et al. | |
| 2005/0215874 | A1 | 9/2005 | Wang et al. | |
| 2005/0231729 | A1 | 10/2005 | Lopushansky et al. | |
| 2006/0115202 | A1 | 6/2006 | Stevens et al. | |
| 2008/0097193 | A1 * | 4/2008 | Karmarkar | A61B 5/055 600/423 |
| 2009/0012511 | A1 * | 1/2009 | Welches | A61B 18/201 606/15 |
| 2009/0171238 | A1 * | 7/2009 | Hanley | A61B 5/01 600/549 |
| 2009/0306591 | A1 * | 12/2009 | Amisar | A61M 25/01 604/122 |
| 2010/0066371 | A1 * | 3/2010 | Vij | A61B 5/055 324/318 |
| 2011/0301508 | A1 * | 12/2011 | Sethuraman | A61N 7/022 601/2 |
| 2012/0039357 | A1 | 2/2012 | Levesque et al. | |
| 2012/0184842 | A1 * | 7/2012 | Boularot | A61B 5/0068 600/411 |
| 2013/0197498 | A1 * | 8/2013 | Laske | A61B 18/02 606/21 |
| 2014/0012155 | A1 * | 1/2014 | Flaherty | A61B 5/015 600/549 |
| 2014/0128881 | A1 * | 5/2014 | Tyc | A61B 18/22 606/130 |
| 2015/0289929 | A1 * | 10/2015 | Toth | A61B 18/1492 600/372 |
| 2015/0297246 | A1 * | 10/2015 | Patel | A61B 17/1671 606/79 |
| 2017/0143214 | A1 * | 5/2017 | Garibotto | A61B 5/6852 |

OTHER PUBLICATIONS

Biopac Systems Inc.; Phychophysiology: Fiber Optic Temperature Rectal Probe; product description http://www.biopac.com/Research.asp?Pid=4892 accessed Aug. 17, 2012.

Budelmann, C., et al.; Electronic Sensor Nodes Powered over Fibre Optimized for Ultra-Precise Temperature Measurements in Magneticresonance Imaging Machines; 2012; 1st Joint International Symposium on System Integrated Inelligence; vol. 1; pp. 189-191.

De Jonckheere, J., et al.; OFSETH: Optical Fibre Embedded into technical Textile for Healthcare, an efficient way to monitor patient under magnetic resonance imaging; 2007; IEEE EMBS; pp. 3950-3953.

Nasr, V. G., et al.; Performance Validation of a Modified Magnetic Resonance Imaging-Compatible Temperature Probe in Children; 2012; Anesthesia & Analgesia; 114(6)1230-1234.

Park, Y.-L., et al.; MRI-compatible Haptics: Strain sensing for (56) References Cited

OTHER PUBLICATIONS real-time estimation of three dimensional needle deflection in MRI environments; 2009; Int'l. Proc. MRM; vol. 17:63.

Sonmez, M., et al.; MRI active guidewire with an embedded temperature probe and providing a distinct tip signal to enhance clinical safety; 2012; Journal of Cardiovascular Magnetic Resonance; 14:38.

* cited by examiner

REUSABLE MR SAFE TEMPERATURE PROBE FOR SURFACE AND BODY TEMPERATURE MEASUREMENT

CROSS REFERENCE TO RELATED APPLICATIONS

This application is a national filing of PCT application Serial No. PCT/IB2013/060765, filed Dec. 10, 2013, published as WO 2014/097049 A2 on Jun. 26, 2014, which claims the benefit of U.S. provisional application Ser. No. 61/738,460 filed Dec. 18, 2012, which is incorporated herein by reference.

The following relates generally to magnetic resonance imaging and temperature sensing. It finds particular application in conjunction with non-ferrous sterile temperature sensing, and will be described with particular reference thereto. However, it will be understood that it also finds application in other usage scenarios and is not necessarily limited to the aforementioned application.

During magnetic resonance (MR) imaging, patient vital signs are frequently monitored such as the temperature of a patient. Monitoring can include a surface temperature with a probe placed against the skin of the patient or internally in the gut such as through the esophagus or the rectum. Temperature can also be used as part of an imaging protocol where temperature can affect quantitative measurement such as diffusion rates in angiograms.

Safe temperature probes in magnetic resonance imaging ideally use non-conductive, non-ferrous materials. Magnetic resonance uses strong radio frequency (RF) and gradient magnetic fields which can induce currents in conductive materials. Ferrous materials can cause aberrations in magnetic fields. Conductive materials with induced currents can cause unsafe conditions for the patient such as the potential for patient burns.

The material used during magnetic resonance imaging should not affect the imaging. That is, the material should be invisible to the magnetic resonance imaging and not emit proton resonance. Improper selection of materials can cause distortions or gaps in the MR signals which cause distortions or gaps in the MR images.

The protocols and procedures used before, during, and after magnetic resonance imaging vary and accommodate a wide variety of situations that call for flexibility of the temperature probe. For example, a surface temperature may be all that is called for by one situation, while a different patient protocol may call for an internal temperature. In order to provide an efficient and effective workflow, the workflow and tools used for MR imaging should accommodate the variety of situations with minimal change in tools such as the temperature probe. The time to measure the temperature is called the response time and includes the time from the application of the probe to the body surface or internally to the time of temperature measurement. The response time is based on the material properties including thickness used to measure the temperature. The response time affects the clinical workflow. Too long a response time is undesirable in measuring patient vital signs and/or measuring changes for a clinical protocol and may pose a risk to the patient.

For internal usage, the probe is sterile and biocompatible. Typically, MR probes used internally are disposable because of the difficulty of sterilization for reuse. For example, a fiber optic probe such as a single piece Fabry-Perot optical sensor can be used in MR imaging, but the materials in the probe are not easily sterilized. Heat is one method of sterilization which is not compatible with fiber optics. Alternatively, chemicals and/or abrasives can be used, but can also damage the fiber optics. Typically, fiber optic temperature probes, although expensive, are used as disposable probes.

Probe materials of an internal probe are often bent to pass through the nasal passage into the esophagus. The probe needs to accommodate the size and bending within the small nasal passage during insertion and removal. A stiff probe can damage the cavity and harm the patient. The probe during insertion and removal should be strong enough not to break or leave components in the patient. The sterile portion of a probe which is inserted into the patient can be as long as 50 cm.

The following discloses a new and improved reusable MR safe probe which addresses the above referenced issues, and others.

In accordance with one aspect, a magnetic resonance probe includes a fiber optic sensor probe and a sheath. The fiber optic sensor probe includes a non-ferrous sensor on a distal portion configured for insertion into a subject, a locking element connected to the distal portion, and a proximal portion connected to the locking element and in light communication via an optical fiber with the non-ferrous sensor and includes a connector. The sheath covers the distal portion of the fiber optic sensor probe, engages the locking element, and provides a sterile outer surface.

In accordance with another aspect, a sterile sheath includes a tube of a material which produces no magnetic resonance signal and configured with a cavity open at one end and to receive and enclose at least one non-ferrous sensor located at an end of a fiber optic sensor probe, closed at an other end, and which provides a sterile outer surface.

In accordance with another aspect, a method for configuring a magnetic resonance temperature probe includes inserting a non-ferrous temperature sensor on a distal portion of a fiber optic sensor probe into a sterile sheath which produces no magnetic resonance signal and covers the distal portion of the fiber optic sensor probe, and the proximal end of the sheath frictionally engages a locking element connected to the distal portion of the probe.

One advantage is a sterile temperature probe which is MR safe and reusable.

Another advantage resides in accommodating surface and internal uses with a single probe.

Another advantage resides in the material size, flexibility, and strength for internal usage.

Another advantage resides in ease of use in an MR clinical workflow.

Another advantage resides in the disposable sterile sheath.

Another advantage resides in the coupling of the disposable sterile sheath and the fiber optic temperature probe.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
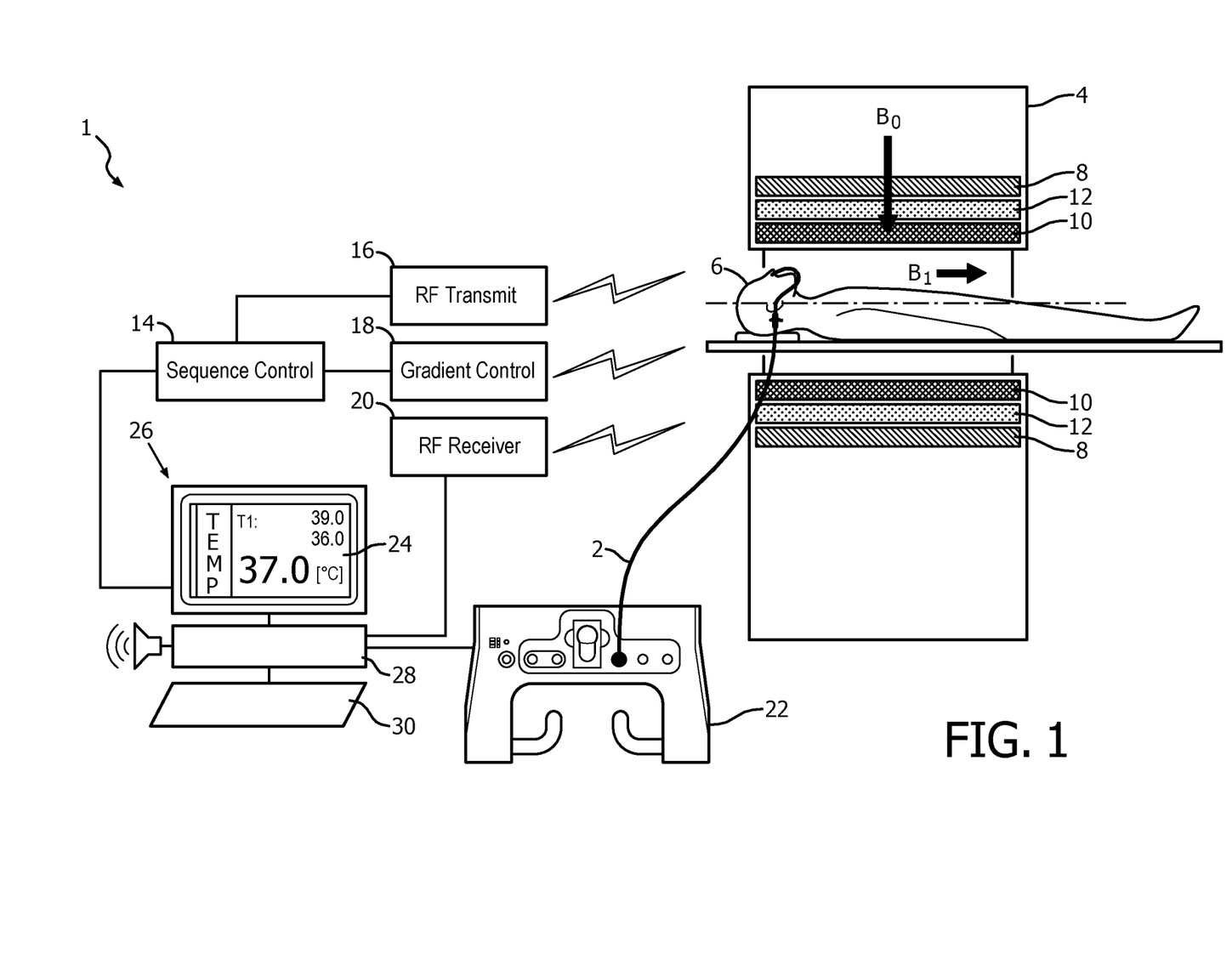
FIG. 1 schematically illustrates an embodiment of a magnetic resonance system with a reusable MR safe probe.

With reference to FIG. 1, an embodiment of a magnetic resonance system 1 with a reusable MR safe probe 2 is schematically illustrated. The system 1 includes a MR scanner 4 such as an open system or c-type scanner, a horizontal bore scanner, and the like shown in a cross section view. The scanner includes an opening or bore that defines an examination region in which a subject 6 is placed for a spectroscopic and/or imaging examination. The MR scanner 4 includes one or more main magnets 8 with a C-shape ferrous flux return path, one or more radio frequency (RF) coils 10, and one or more gradient coils 12.

The system 1 includes a sequence controller 14 which controls the operation of the imaging sequence, a RF transmitter unit 16 controlling the operation of the RF coils 10, and a gradient controller 18 controlling the operation of the gradient coils 12. The communication between the controlling unit and the corresponding coils can be wireless or wired. The RF coils 10 generate radio frequency pulses which excite and manipulate resonance in tissue of the subject 6. The RF coils 10 can include a whole body coil and/or a local coil such as a torso coil, hand coil, shoulder coil, knee coil, etc. The one or more gradient coils 12 generate gradient magnetic fields across the static magnetic field to spatially encode the induced resonance, induced gradient echoes, and the like. The sequence controller 14 configures the RF coils and the gradient coils to excite and manipulate resonance in tissues of the subject.

The system 10 includes a RF receiver unit 20, which receives MR signals. As the resonance decays in the tissue of the subject, weak radio frequency signals or MR signals are received by a radio frequency antenna such as the RF coils 10 and transmitted to the RF receiver unit 20. A reconstruction unit, such as a processor, receives RF data or MR signals from the RF receiver 20 and reconstructs one or more images from the received MR data such as image slices, a volume, etc.

The reusable MR safe probe 2 can be used during a MR imaging procedure or in the presence of the MR scanner 4 at any time. The reusable MR safe probe can be used internally by insertion into the gut of the subject 6 such as either through the nasal passage into the esophagus or the rectum. The reusable MR safe probe has flexibility and size to bend around and pass through the nasal passages of the subject. The reusable MR safe probe 2 includes material which produces no or a minimal MR signal, e.g. emits no proton resonance during excitation or in the presence of the magnetic fields generated by the main magnet coils 8 or the gradient coils 12. The portion of the probe 2 which is inserted into the subject includes an outer surface which is sterile and non-permeable, and includes at least one non-ferrous sensor such as a temperature sensor. The reusable MR safe probe connects to a console 22 which receives the light signal from the temperature sensor and converts the signal to a human readable quantified measurement which is displayed on a display device 24 and/or used in conjunction with analysis of the received MR signals.

The display device 24 can be a separate device such as an LED display or incorporated into a workstation 26. The workstation 26 includes an electronic processor or electronic processing device 28, the display device 24, and at least one input device 30. The workstation 26 can be a desktop computer, a laptop, a tablet, a mobile computing device, a smartphone, and the like. The display device 24 can include a computer monitor, a touch screen, Cathode ray tube (CRT), Storage tube, Flat panel display, Light-emitting diode (LED) displays, Electroluminescent display (ELD), Plasma display panels (PDP), Liquid crystal display (LCD), Organic light-emitting diode displays (OLED), a projector, and the like. The input device 30 can be a keyboard, a mouse, a microphone, and the like.

The reusable MR safe probe 2 can be configured to receive and display light signals which correspond to a sensed value such as temperature as soon as connected to the console 22. The sensed value such as temperature can include a continuous measurement and the display on the display device 24 updated with the continuous measured values. The processor 28 can be configured with maximum or minimum values for the sensed values which sound an alarm such as an audible sound or visual display.

Figure 2:
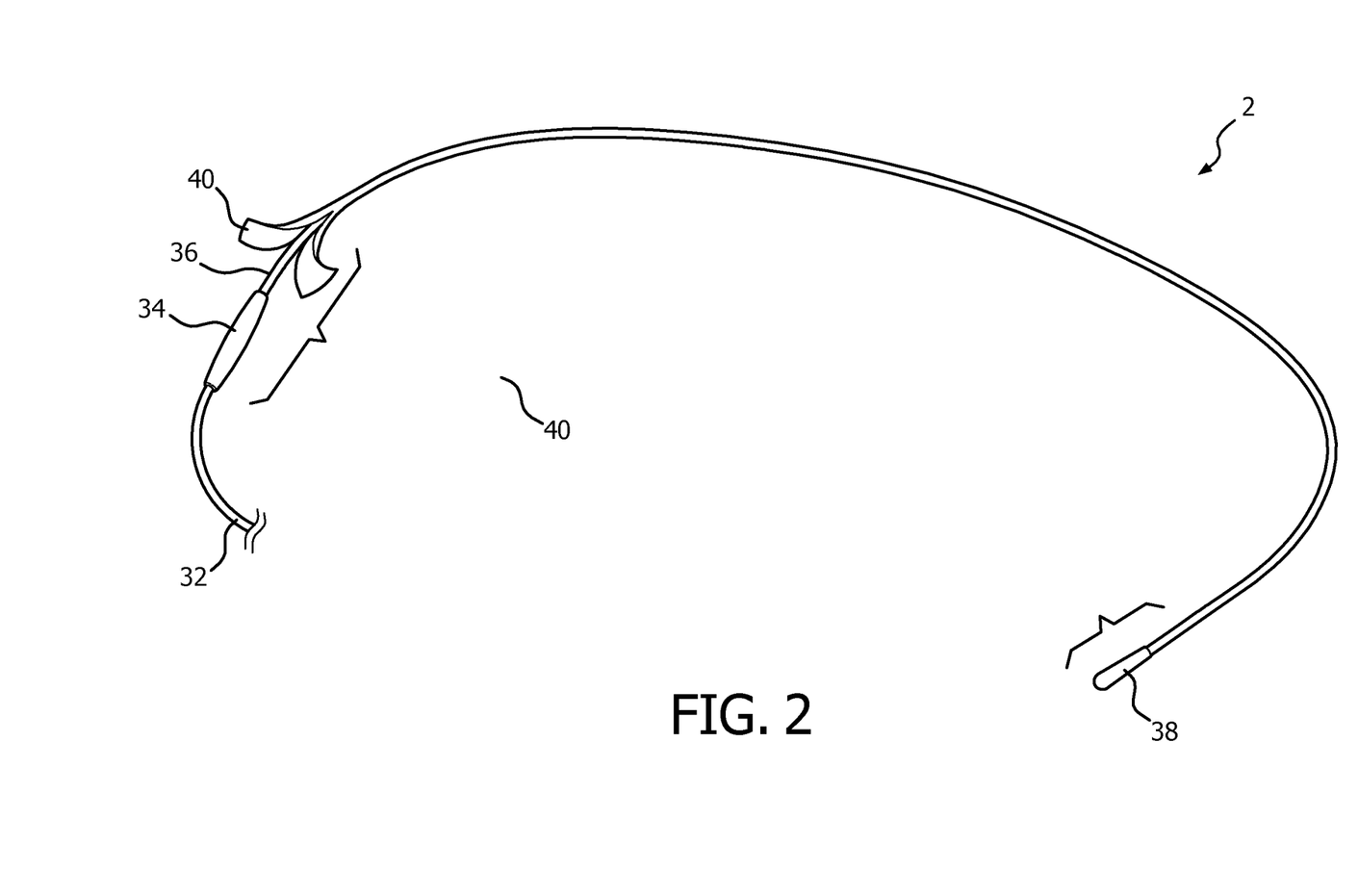
FIG. 2 schematically illustrates one embodiment of a reusable MR safe probe.

With reference to FIG. 2, one embodiment of a reusable MR safe probe 2 is schematically illustrated. The reusable MR safe probe 2 includes a fiber optic sensor probe 32 and a sheath 38. The fiber optic sensor probe 32 is shown with a distal portion 36 and a locking element 34 which engages the sheath 38 when the probe is inserted and indicates the proper depth in the sheath. The probe 32 is shown without the entire proximal portion and a connector. The probe 32 with the sheath 38 includes a maximum diameter which passes through a nasal passage of the subject such as 4.9 mm. The fiber optic sensor probe is reusable. The sheath is disposable. The sheath 38 covers and encloses the distal end of the probe and provides a non-permeable sterile surface.

The sheath in one embodiment includes tabs 40 at the proximal end of the sheath for pulling the sheath onto the probe 32 or holding the sheath while inserting the probe 32 to the indicated depth, and engaging the locking element 34. The tabs can be two opposing tabs which allow a healthcare practitioner to grasp the sheath and handle in a manner which maintains the sterile outer surface. Gripping the tabs and gripping the locking mechanism, opposing forces exerted by the healthcare practitioner can bring the proximal end of the sheath to the locking element and engage the sheath to the locking element, e.g. tightly couple the sheath to the locking element forming a pressure seal. The tabs 40 when pulled toward the distal end of the probe 32 and away from the locking element, assist the healthcare practitioner in removal of the sheath 38 from the probe 32. The sheath during removal can be pulled along the distal portion of the probe 32 by the tabs and fold the outer contaminated surface inside out. The removed sheath turned inside out can be safely handled and properly disposed.

The reusable MR safe probe 2, with the sheath 38 properly engaged with and enclosing distal end of probe 32 that includes the temperature sensor, is inserted into the esophagus or rectum of the subject. The reusable MR safe probe 2 with the sheath 38 and the probe 32 are inserted and removed from the subject as one unit. The sheath provides a sterile non-permeable barrier between the temperature sensing probe 32 and the subject.

In one embodiment, portions of the fiber optic sensor probe 32 and/or the sheath 38 can be manufactured with MR visible material, e.g. emits proton resonance for internal visual monitoring of the probe by the MR system. For example, a thin line in the sheath 38 can indicate the location and/or direction of the reusable MR safe probe 2 in an image reconstruction. The line can be a thin line, dotted line, include arrows, etc. The image reconstruction can show where the reusable MR safe probe 2 is internally in the subject. The portion of the MR visible material can be limited so that the material does not interfere with the image of the subject.

Figure 3A:
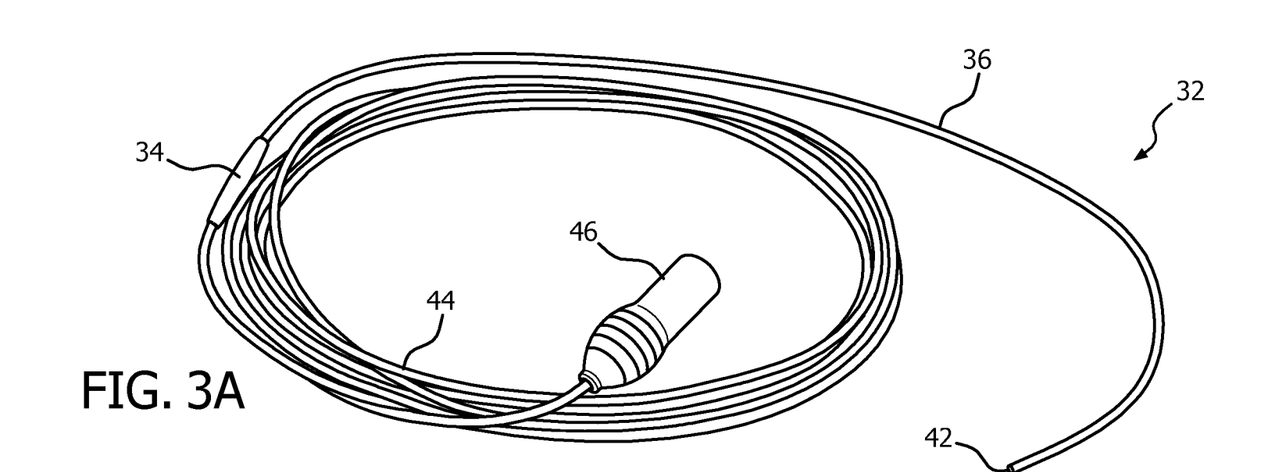
FIGS. 3A-3E schematically illustrate an embodiment of a fiber optic sensor probe.

With reference to FIG. 3A, an embodiment of a fiber optic sensor probe 32 is shown in a perspective view. The locking element 34 divides the probe 32 into the distal portion 36 which includes a temperature sensor 42 and a proximal portion 44 which connects to console via a connector 46. The distal portion 36 has a length of sterile surface such as 50.8-55.8 cm. The proximal portion 44 includes a length from the subject to the console such as 3-5.5 meters.

Figures 3B, 3C, 3D, 3E:
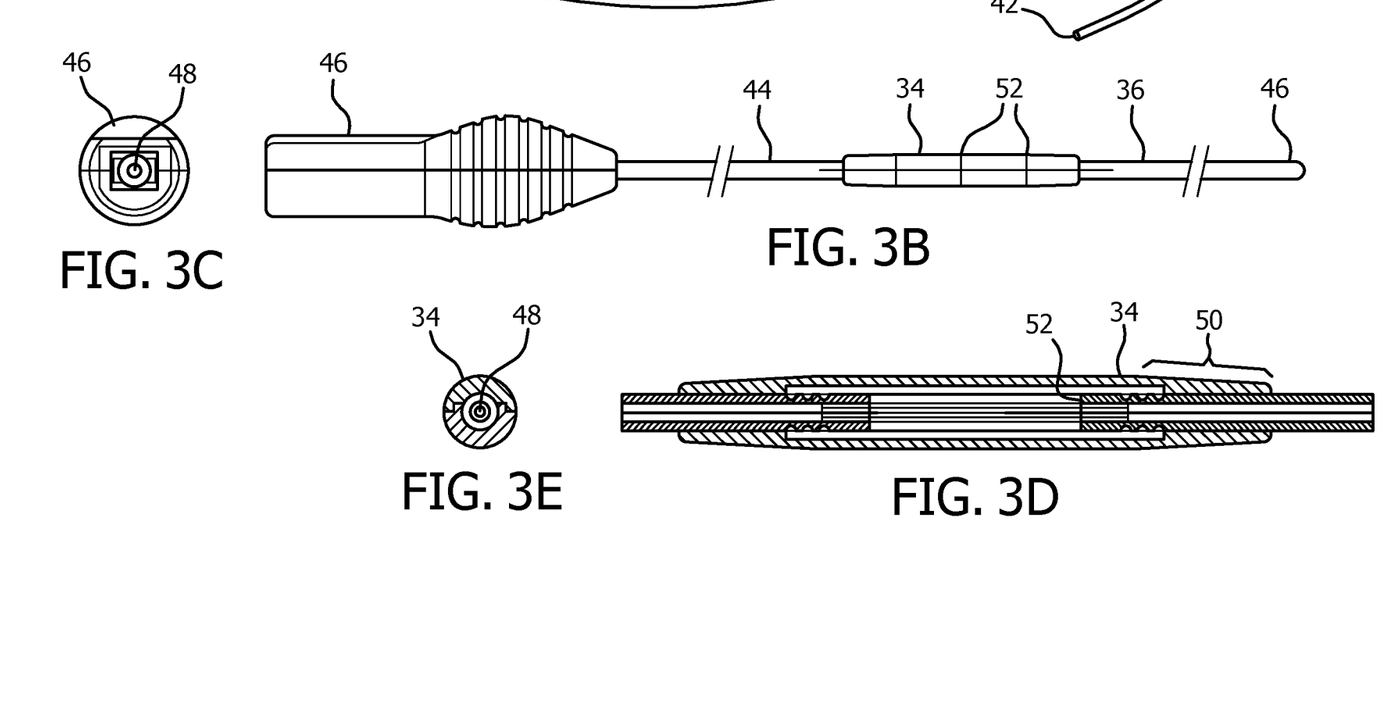

FIG. 3B shows an enlarged side view of fiber optic sensor probe 32. The distal portion 36 includes a temperature sensor 42 and can include a rounded tip. The sensor operates from +20° C. to +44° C.±0.5° C. The proximal portion 44 can include a polyvinyl-chloride (PVC) covered single optical fiber. The proximal portion can be colored blue for visibility. The proximal portion includes a connector 46 which can operate reliably after multiple insertion cycles and in one embodiment meets an IEC 61754 standard e.g. IEC 61754-4. The PVC material, such as DEHP free 85A grey PVC from Sunlight Corporation, produces no visible MR signal, e.g. invisible to MR imaging. The connector 46 connects to the system 1 via a fiber optic connector in the console 22 and can include standard fiber optic connector interfaces. FIG. 3C shows an end view of the connector 46. The single optical fiber 48 is enclosed with the connector and optically connects to the console such that light communication is provided between the temperature sensor 42 and the console 22.

With reference to FIG. 3D, a side view of the locking element 34 is shown in a central slice. The locking element includes a rigid tapered surface 50. The locking element can include marks 52 in the surface and/or lines which indicate the proper distance for insertion of the probe 32 into the sheath 38. The locking element includes a maximum outer diameter which is large the maximum inner diameter of the sheath 38. The length of the locking element can include a length easily gripped by the healthcare practitioner such as 5 cm. The size can be limited by the bulk and weight in handling of the probe by the healthcare practitioner. FIG. 3E shows a cross section view of the locking element 34 with the enclosed single optical fiber 48. Although a single optical fiber for both transmitted and returned light is illustrated, separate transmit and return optical fiber are also contemplated. Further, additional optical fibers may transmit light to and from other biological sensors.

Figure 4:
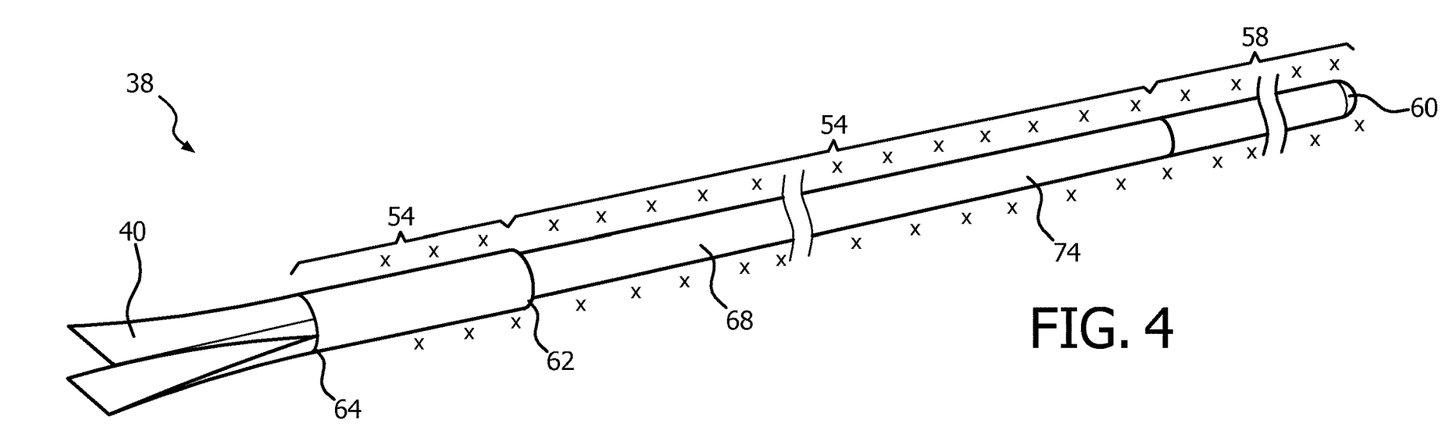
FIG. 4 illustrates an embodiment of a sheath in perspective.

FIG. 4 illustrates an embodiment of the sheath 38 in perspective. The sheath 38 includes a material which produces no MR signal such as TSP 1051-85A polyurethane made by Polyzen. The material emits no proton resonance, e.g. invisible to MR imaging. The material encloses the distal portion 36 of the probe 32, as shown in reference to FIG. 2, in a cavity with one opening and carries the probe 32 within the cavity or opening of the sheath 38. The sheath can be further divided into a proximal portion 54, a central portion 56, and a distal portion 58. The central portion and distal portion provides flexibility and sufficient strength with a thickness such as 0.0381 mm.

The distal portion 58 can include a rounded tip 60. The rounded tip can ease the insertion into the subject as the probe bends and moves through the narrow nasal passage of the subject. The rounded tip can conform to a rounded tip of the probe 32 or provide a rounded tip to the probe 32. The distal portion 58 can include a length such as 20.3 cm with a smaller outer diameter such as 3.9 mm.

The central portion 56 can include a slightly larger outer diameter such as 4.9 mm for a length such as 30.5 cm. The central portion 56 and the distal portion 58 provide an overall length of a sterile outer surface such as 50.8 cm.

The proximal portion 54 includes a rigid or thickened tubular connection 62 to the central portion. The proximal portion includes an outer diameter with firmness and tear resistance to engage the tapered locking element 34 of the fiber optic sensor probe 32 such as 6.04 mm. The proximal portion extends for a length such as 25.4 mm which provides sufficient area to engage the locking element 34.

Two opposing flaps or tabs 40 connect to the proximal end 64 of the proximal portion 54. The tabs extend for a length such as 2.5 cm with a flare such as 9.4 mm for easy gripping by the healthcare practitioner. For example, the healthcare practitioner can grip the proximal end of the locking element 34 of the probe 32 in one hand and grip a tab either side of the sheath in the other. Using opposing forces the sheath can be drawn onto the distal end of the probe 32 or the sheath can be held stationary while the distal end of probe 32 is pushed into the sheath. The proximal portion 54 is pulled by the tabs onto the tapered surface 50 of the locking element 34 to be stretched in a friction locking interaction.

Figure 5:
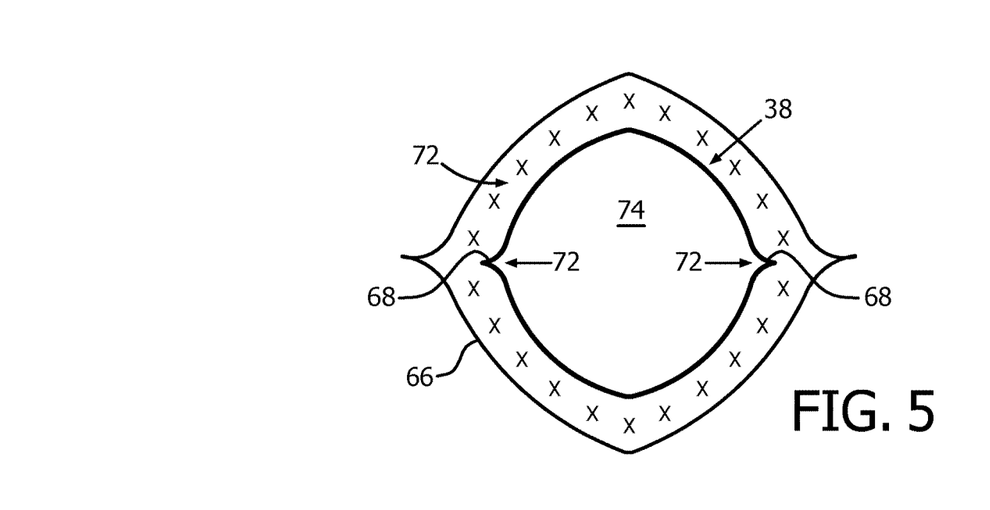
FIG. 5 illustrates an embodiment of a sheath with a cover in a cross section view.

FIG. 5 illustrates an embodiment of the sheath 38 with an optional cover 66 in a cross section view. The sheath includes at least one perimeter seam 68. The perimeter seam is formed to the outside surface. In one embodiment, two perimeter seams are formed opposite. The perimeter seams seal the material of the sheath to provide a sterile outer surface 70. The optional cover 66 such as a peel away introducer with a sterile inner surface can be for an individual sheath. The perimeter seam formed to the outside includes an air channel 72 on the inside which allows air to escape during insertion. By allowing the air to escape, a potential thermal barrier of trapped air is eliminated. A thermal barrier of trapped air can affect the temperature reading by the sensor 42. The at least one perimeter seam also forms the cavity 74 which carries the distal portion of the probe 32 and includes the central 56 and distal 58 portions of sheath 38.

Figure 6:
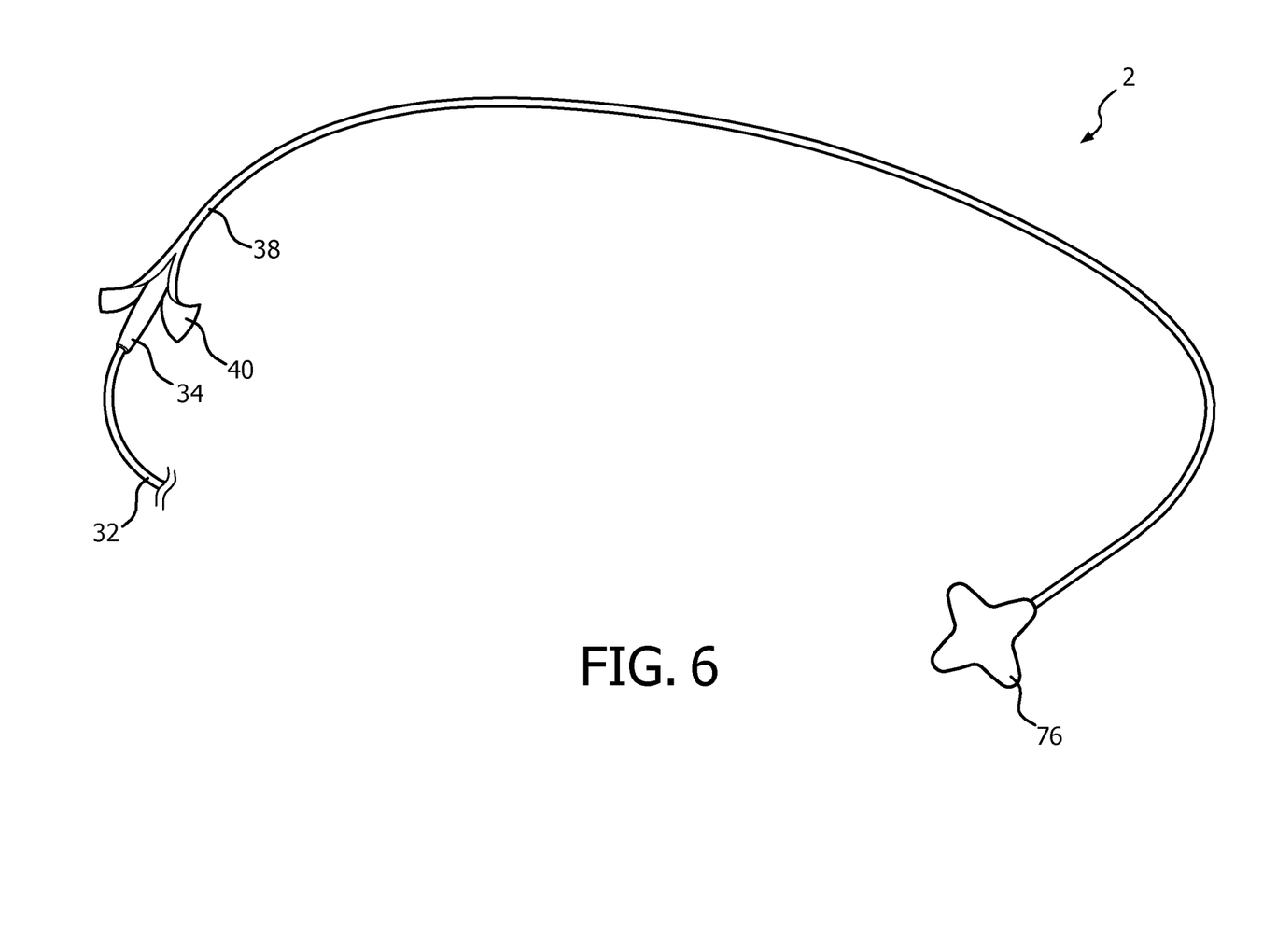
FIG. 6 illustrates an embodiment of the reusable MR safe probe with a surface application.

With reference to FIG. 6 an embodiment of the reusable MR safe probe 2 with a surface application is illustrated. The distal portion of the probe 32 is fully inserted into the sheath 38 and the locking element 34 engages the proximal portion 54 of the sheath 38. The tabs 40 extend over the locking element. An applicator 76 such as an adhesive backed biocompatible material is applied over the tip of the reusable MR safe probe 2 and affixed to the skin surface of the subject 6. During removal, the applicator 76 and the sheath 38 can be disposed of as a unit. By using the sheath, any adhesive adheres to the sheath 38 and not the surface of the probe 32, which avoids potential damage with the removal of any adhesive from the reusable probe 32.

Figure 7A:
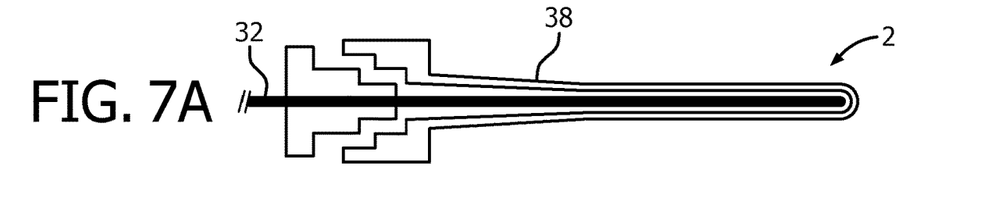
FIGS. 7A-7M diagrammatically illustrate various embodiments of the reusable MR safe probe and sheath.
Figure 7B:
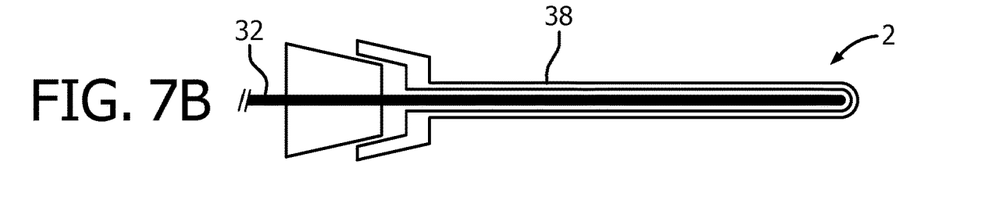
Figures 7C, 7D:
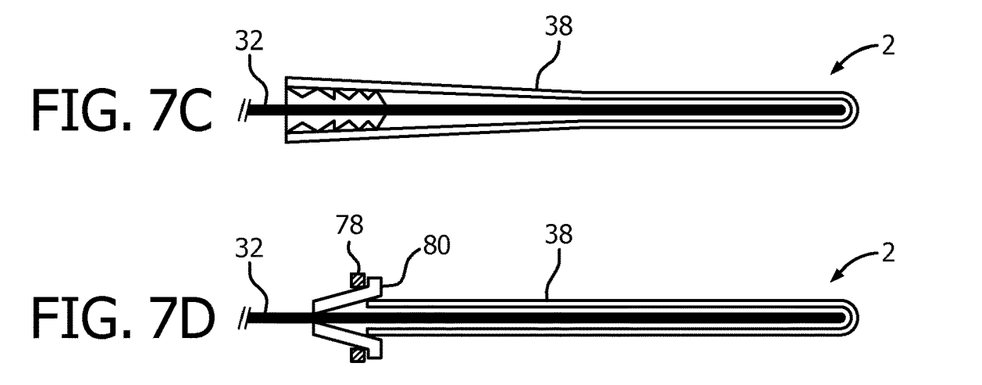
Figure 7E:
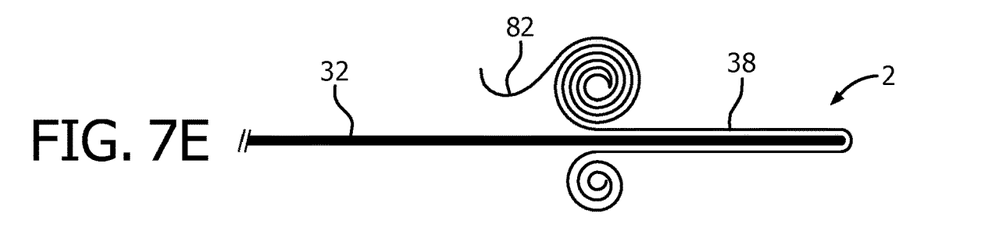
Figure 7F:
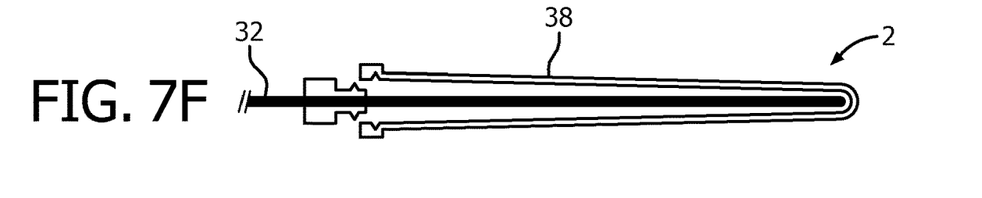
Figure 7G:
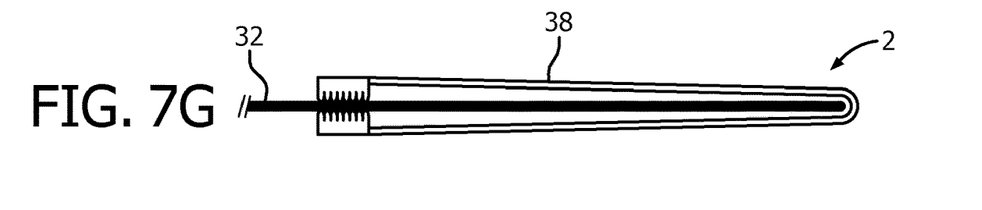
Figure 7H:
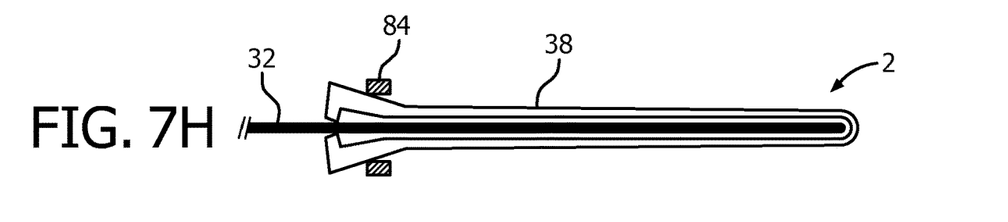
Figure 7I:
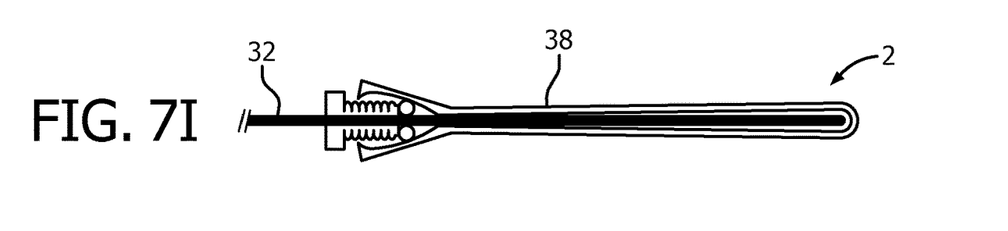
Figure 7J:
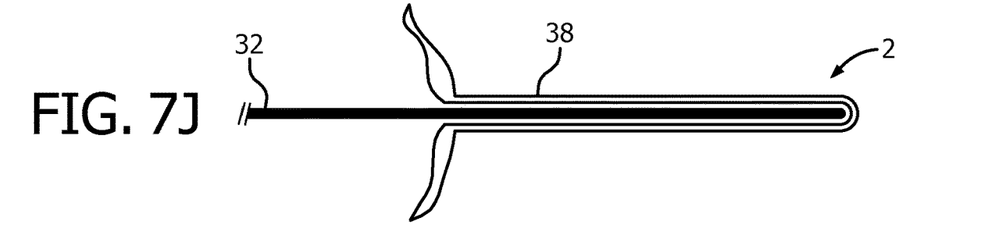
Figure 7K:
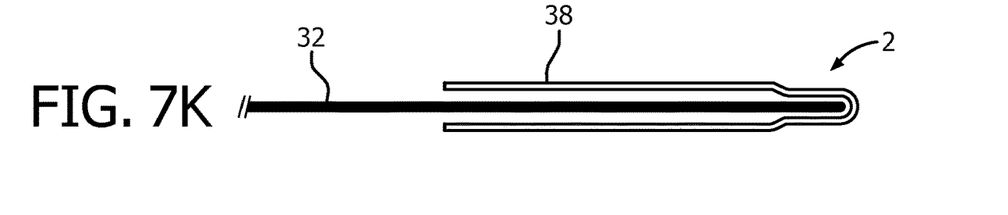
Figure 7L:
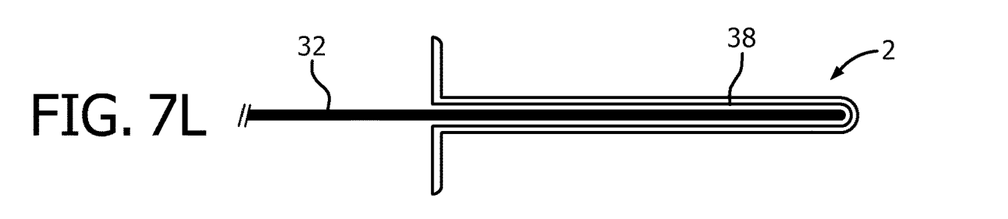
Figure 7M:
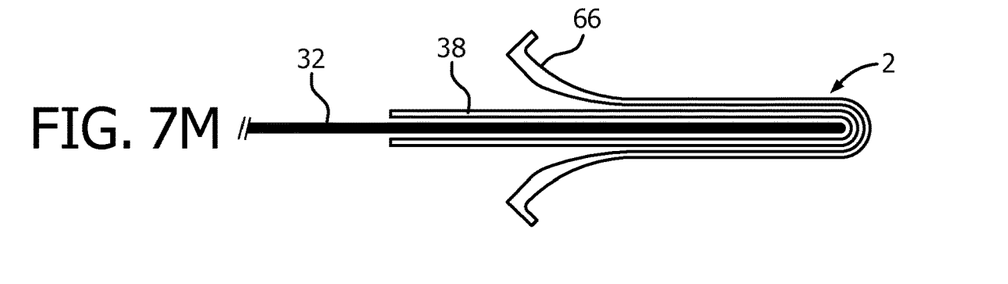

FIGS. 7A-7M diagrammatically illustrate various embodiments of the reusable MR safe probe 2. In FIG. 7A, the probe 32 and the sheath 38 include a stepped locking element. The distal end of the sheath has mating steps which frictionally engage the steps of the locking element. FIG. 7B shows a tapered locking element of both the probe 32 and the sheath 38. The tapered locking element on the probe 32 expands to a larger diameter than the tapered locking element located on the proximal end of the sheath 38. The tapered locking element located on the proximal end of the sheath engages frictionally the tapered locking element of the probe. A barbed locking element on the probe 32 is shown in FIG. 7C. The straight or flared sheath 38 slides over the barbed locking element on the probe and engages with the barbed locking element with friction. A plastic collet 78 on the probe 32 in FIG. 7D engages and holds the sheath 38. A locking ring 80 clamps the collet tight around the proximal edge of the sheath. The locking ring slides from the proximal towards the distal end to lock the collet. The sheath 38 is rolled onto the probe 32 using a draw string 82 in FIG. 7E. The sheath is rolled by pulling the draw string towards the proximal end of the probe and unrolls the sheath with a tight fit onto the probe. A locking element is threaded on the probe 32 and the sheath 38 in FIG. 7F. The probe is inserted into the sheath and with a twisting motion such as with a screw, the female portion located on the sheath engages the male portion locking element of the probe. In FIG. 7G, a barbed locking element is included in the sheath 38. The probe is inserted into the sheath and pulled with the locking element of the sheath frictionally engaging the straight surface of the probe. The sheath 38 includes the plastic collet in FIG. 7H. A locking ring 84 slides over the plastic collet incorporated into the proximal end of the sheath. The ring slides from the distal to the proximal end. The sheath 38 includes a crushable band in FIG. 7I. The probe includes a rough surface which frictionally engages the sheath after crushing. The sheath 38 includes one or more tails in FIG. 7J which are tied around the probe 32. The sheath is pulled over the probe and the tails are tried around the probe to hold the sheath in position. The sheath 38 includes a length of decreased diameter near the tip which prevents the sensor 42 on the distal portion of the probe 32 from slipping out in FIG. 7K. The sheath is pulled onto the probe and the remainder of the sheath can be increased in thickness which increases the rigidity of the remaining portion. The sheath 38 in FIG. 7L includes a flange to assist gripping by the healthcare practitioner during insertion of the probe 32 into the sheath. The flange provides a rigid surface which extends radially from the proximal end of the sheath. The sheath 38 in FIG. 7M includes a cover 66 such as a peel away introducer. The introducer includes tabs which provide a gripping surface. The healthcare practitioner grasps the tabs and pulls the sheath onto the probe. After the probe is fully inserted into the sheath, the introducer is peeled away leaving the sheath covering the distal end of the probe.

Figure 8:
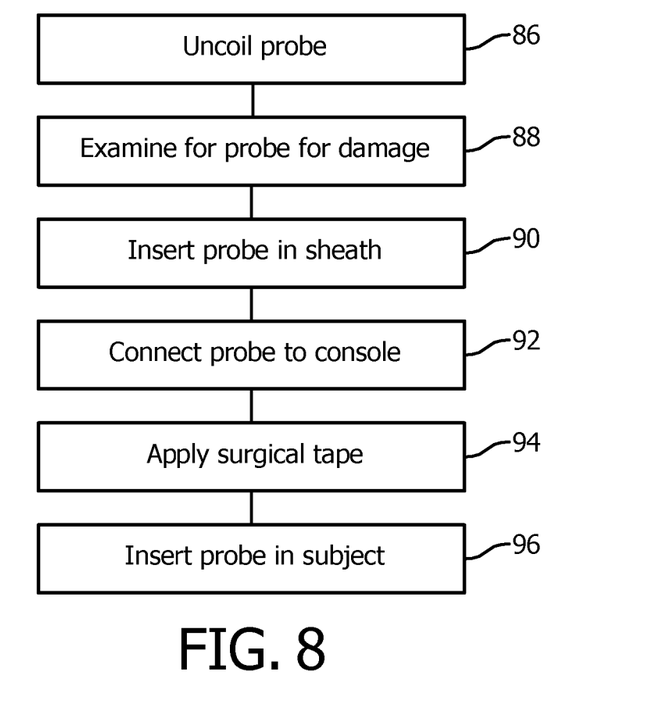
FIG. 8 flowcharts one method of configuring the reusable MR safe probe for insertion into a subject.

With reference to FIG. 8 one method of configuring the reusable MR safe probe 2 for insertion into a subject 6 is flowcharted. In a step 86, the probe 32 is uncoiled. The uncoiling avoids knotting or kinking the probe 32. In a step 88, the healthcare practitioner examines the probe 32 for damage, adhesives or residue.

In a step 90, the healthcare practitioner inserts the probe 32 into the sheath 38. The healthcare practitioner holds the tabs 40 of the sheath 38 and pulls the sheath completely over the distal portion 36 of the probe 32 until the locking element 34 of the probe 32 is fully seated into or engaged with the proximal end 64 of the sheath 38 and the two opposing tabs 40 rest over the locking element 34. In embodiments with an additional locking element, the locking element is engaged when the sheath is properly seated, the distal portion of the probe 32 fills the sheath completely to the tip, e.g. no open cavity with air at the end of the sheath. The step can include removal of an optional cover 66 such as a peel away introducer. The reusable MR safe probe 2 is connected to the system 1 via the console 22 with the connector 46 in a step 92. Connecting to the console 22 can initiate sensor or specifically temperature readings. In an optional step 94, surgical tape can be applied to the tabs 40 and around the locking element 34.

The reusable MR safe probe 2 with a sterile outer surface is inserted into the subject 6, e.g. through a nasal passage or rectum in a step 96. The probe 2 provides sensor readings with light communications via an optical fiber 48 using a non-ferrous sensor 42 and does not include conductive elements such as ferrous sensors or conductive wires. The absence of conductive elements such as ferrous sensors or conductive wires eliminates the potential hazard of burns to the subject. The material of the probe 2 produces no MR signal, e.g. invisible to MR imaging, which eliminates potential distortions or gaps in imaging. The biocompatible sterile outer surface of the probe 2 allows usage internally to a subject 6.

Figure 9:
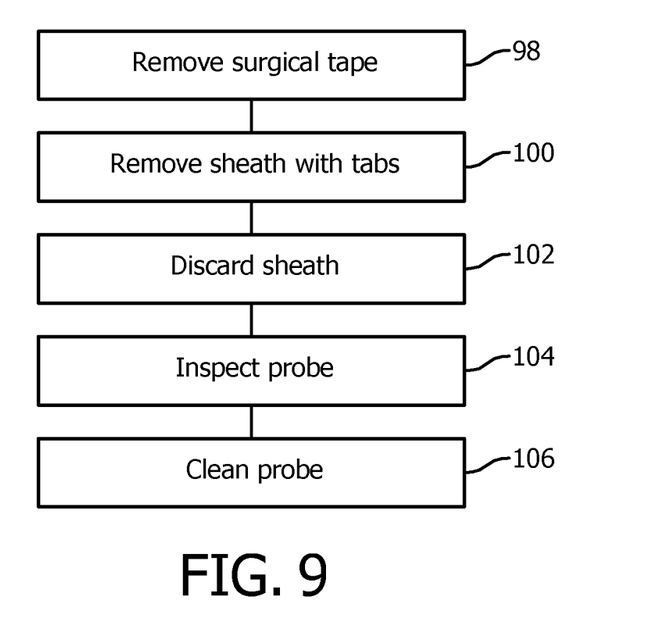
FIG. 9 flowcharts one method of removing the sheath from the reusable MR safe probe.

FIG. 9 flowcharts one method of removing the sheath 38 from the reusable MR safe probe 2. In a step 98, surgical tape is removed from around the tabs 40 if surgical tape was previously applied. The sheath is removed in a step 100. The healthcare practitioner grips the tab or tabs 40 of the sheath 38, and the proximal end of the locking element 34 of the probe 32. With opposing force the sheath 38 is pulled from the probe 32 while turning the contaminated outer surface of the sheath 38 inside out. In a step 102, the sheath is properly discarded according to a facility's biohazard procedures.

In a step 104, the probe 32 is inspected by the healthcare practitioner, which ensures that the sheath was completely removed from the probe 32. The probe 32 is cleaned and/or disinfected in a step 106.

Figure 10:
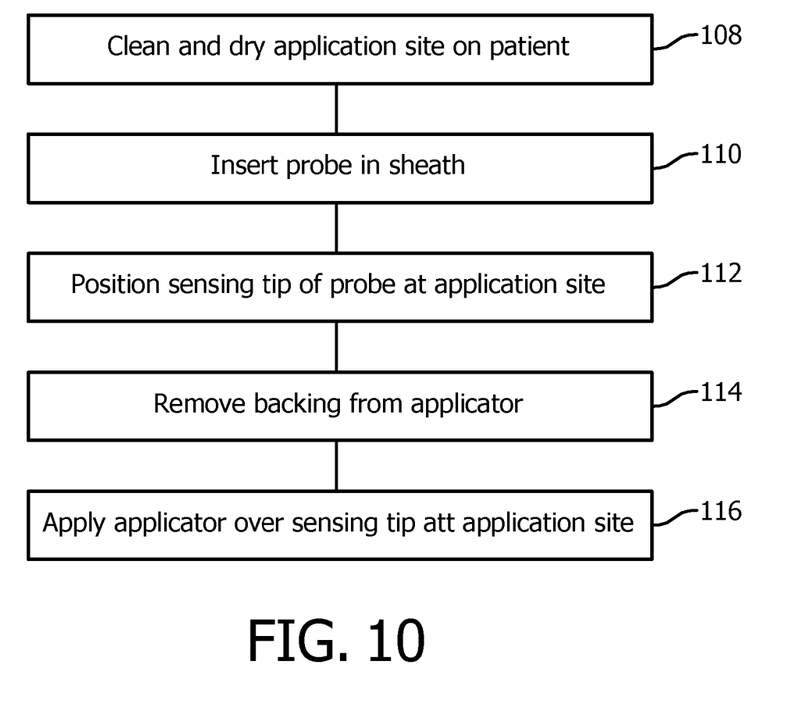
FIG. 10 flowcharts one method of configuring the reusable MR safe probe for a surface application.

With reference to FIG. 10 one method of configuring the reusable MR safe probe 2 for a surface application is flowcharted. In a step 108, the healthcare practitioner cleans and dries the application site on the subject 6. In a step 110, the healthcare practitioner inserts the fiber optic sensor probe 32 into the cavity of the sheath 38 by gripping the tabs 40 and pulling the sheath onto the distal portion of probe 32 until fully engaged by the locking element 34 of the probe 32.

The healthcare practitioner positions the sensing tip of the reusable MR safe probe 2 at application site of the subject 6 in a step 112. The backing is removed from an applicator 76 in a step 114. The applicator 76 with the backing removed is applied over the sensing tip of the reusable MR safe probe 2 at application site of the subject 6 in a step 116.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A magnetic resonance probe configured for both insertion into and application to a surface of a subject, the magnetic resonance probe comprising:
    a reusable fiber optic sensor probe comprising:
        a distal portion having a sensor end and a locking element end opposite from the sensor end;
        a proximal portion;
        a locking element connecting the locking element end of the distal portion to the proximal portion, wherein the locking element comprises a tapered rigid surface and an indicator that indicates a proper distance for sheath insertion;
        a non-ferrous sensor on the sensor end of the distal portion; and
        an optical fiber connected with the non-ferrous sensor, the optical fiber extending from the proximal portion to the non-ferrous sensor;
    a disposable sheath having a non-permeable sterile outer surface, a closed end and an open end opposite from the closed end, wherein the closed end covers the sensor end of the fiber optic sensor probe so that the distal portion of the fiber optic sensor probe fills the sheath, wherein the open end of the sheath comprises pull tabs, and wherein a portion of the open end of the sheath engages with the locking element at or near the indicator; and
    a removable applicator configured to affix the closed end of the sheath to a surface of a subject.

2. The magnetic resonance probe according to claim 1, wherein the closed end of the sheath comprises a rounded tip.

3. The magnetic resonance probe according to claim 1, wherein the sheath further comprises:
    at least one perimeter seam located on the outside of the sheath which provides enclosure of a central portion and a distal portion of the sheath about a cavity which carries the distal portion of the fiber optic sensor probe.

4. The magnetic resonance probe according to claim 1, wherein the pull tabs are configured to allow a healthcare practitioner to remove the sheath from the fiber optic sensor probe while turning a central portion and a distal portion of the sheath inside out.

5. The magnetic resonance probe according to claim 1, wherein the material of the fiber optic sensor probe and the sheath produce minimal magnetic resonance signal.

6. The magnetic resonance probe according to claim 1, wherein the non-ferrous sensor includes a temperature sensor configured to measure a temperature change from 20 C-37 C in 20 seconds or less.

7. The magnetic resonance probe according to claim 1, wherein
    the sheath includes a tube of a material which produces no magnetic resonance signal.

8. The magnetic resonance probe according to claim 7, wherein the tube comprises:
    a tubular proximal portion connected to the open end of the material which engages and connects with a locking element of the sensor probe.

9. The magnetic resonance probe according to claim 7, wherein the material comprises at least one perimeter seam which runs the length of the cavity on the outside of the cavity and provides an air channel on the inside of the at least one perimeter seam.

10. The magnetic resonance probe according to claim 7, wherein the sheath is at least 50.8 cm long and less than 4.9 mm in diameter.

11. The magnetic resonance probe according to claim 7, further comprising:
    a removable cover which covers and maintains the sterile outer surface of the material.

12. The magnetic resonance probe according to claim 7, wherein the sheath engages the probe with a tapered friction fit.

13. The magnetic resonance probe of claim 7, wherein:
    the fiber optic sensor probe comprises a fiber optic temperature sensing catheter including a temperature sensing probe and an elongated shaft carrying at least one optical fiber.

14. The magnetic resonance probe of claim 13, wherein the elongated shaft has one or more magnetic resonance visible markings.

* * * * *